(12) United States Patent
Withiam et al.

(10) Patent No.: US 7,163,669 B2
(45) Date of Patent: Jan. 16, 2007

(54) COSMETIC COMPOSITIONS COMPRISING CALCIUM SILICATES

(75) Inventors: Michael C. Withiam, Landenberg, PA (US); Donald P. Conley, Conowingo, MD (US); Robert S. Zonis, Belcamp, MD (US)

(73) Assignee: J.M. Huber Corporation, Edison, NJ (US)

( * ) Notice: Subject to any disclaimer, the term of this patent is extended or adjusted under 35 U.S.C. 154(b) by 0 days.

(21) Appl. No.: 10/175,464

(22) Filed: Jun. 19, 2002

(65) Prior Publication Data

US 2003/0235597 A1  Dec. 25, 2003

(51) Int. Cl.
*C01B 33/26* (2006.01)
*C01B 33/20* (2006.01)
*A61K 6/00* (2006.01)

(52) U.S. Cl. .................. 423/327.1; 423/326; 424/401; 514/937

(58) Field of Classification Search ................ 424/401, 424/489, 490, 501; 423/331
See application file for complete search history.

(56) References Cited

U.S. PATENT DOCUMENTS

| 4,557,916 A | 12/1985 | Withiam |
| 5,618,522 A * | 4/1997 | Kaleta et al. ................. 424/60 |
| 5,658,579 A | 8/1997 | LaFleur et al. |
| 5,683,706 A | 11/1997 | LaFleur et al. |
| 5,780,020 A | 7/1998 | Peterson et al. |
| 5,853,899 A * | 12/1998 | Anderson et al. ........... 428/507 |
| 6,444,745 B1 * | 9/2002 | Kilgour et al. ............. 524/588 |
| 6,524,598 B1 * | 2/2003 | Sunkel et al. ............... 424/401 |
| 2003/0108498 A1 * | 6/2003 | Stephens et al. ............. 424/63 |

FOREIGN PATENT DOCUMENTS

| EP | 0 192 276 | 1/1989 |
| WO | WO 97/04737 | 2/1997 |
| WO | WO 00/35413 | 6/2000 |

OTHER PUBLICATIONS

European Journal of Dermatology, Sebum Rhelogy Evaluated by a Two Method *in vivo*. Split—face Study of the Effect of a Cosmetic Formulation; vol. 9, issue 6, Sep. 1999, 455 Investigative Reports.
Japanese Abstract: Daiichi Kurooda Kemikaruzu Chiyoda Kagaku Kenkyusho:Lkk; Preparation of Powdery Solid Cosmetic, JP57072906 A; Application No., 55148823 JP55148823 JP Filed Oct. 23, 1980, A1 Published May 7, 1982.
Japanese Abstract: Pola Kasei Kogyo KK; Cosmetic compositions having good feel and perfume holding properties contain metal silicate, carbonate, tungstate, oxide or hydroxide in form of fine globular substance; JP 54163830 A UPAB Sep. 2, 1999.

* cited by examiner

*Primary Examiner*—Sreeni Padmanabhan
*Assistant Examiner*—Gina C. Yu
(74) *Attorney, Agent, or Firm*—David Mitchell Goodrich; Carlos Nieves; William Parks (57) ABSTRACT

Disclosed is a fluid cosmetic composition comprising a sebum-absorbing calcium silicate. These cosmetic compositions provide effective, long-lasting facial cosmetic coverage that is highly resistant to the sebum-caused deterioration that results in the discoloration and fading typically experienced by conventional cosmetic compositions after a sustained period of use. The cosmetic composition may be in the form of a créme, lotion, gel, semi-solid, dispersion, suspension, foam, mousse or spray.

1 Claim, 5 Drawing Sheets

COSMETIC COMPOSITIONS COMPRISING CALCIUM SILICATES

BACKGROUND OF THE INVENTION

Skin is the largest organ of the body, accounting for almost a fifth of the weight of a normal adult. The skin performs the vital function of separating the internal components of the body from the outside environment, while also providing a permeable membrane to protect and maintain the internal organs.

Located throughout the dermal layer of skin, just below its surface, are sebaceous glands, which secrete a material composed primarily of waxes and lipids, known as "sebum". Sebum acts to moisturize the skin in order to keep it supple and firm, and yet also sufficiently flexible to accommodate the various joints and irregular contours of the body's skeleton and internal organs. Sebum is also believed to provide certain antimicrobial benefits against airborne microbes to prevent the transmission of disease from the outside environment into the body.

While sebum performs these functional skin benefits, it also affects the aesthetic appearance of the skin. For example, the most common cause of acne is a disruption in the normal, continuous flow of sebum that is typically the result of obstructed sebaceous glands. Indeed the principal objective in anti-acne therapy is to clear existing lesions and prevent the formation of new ones. An additional objective of such skin treatment is the removal of excess sebum from the skin.

In addition to contributing to the development of skin-blemishing acne, sebum can also compromise the desired facial appearance that women seek to obtain by using cosmetics, especially facial cosmetics. Women who have imperfect complexions or whose skin appears to have an oily sheen due to the accumulation of sebum often apply a layer of facial cosmetics, known commercially as foundation, or foundation makeup, in order to give the skin a more desirable appearance. However, these cosmetics absorb sebum from the skin, causing the facial cosmetic layer to either take on a shine or become darker, giving the skin a spotty, blotched appearance. In fact, in some cases, an individual's sebum production is so high that it liquefies the cosmetic pigment layer, resulting in a rapid removal of the facial cosmetic either by physical friction and abrasion or by liquid flow. This problem is particularly acute on the eyelid as well as immediately below the eye. In order to avoid this it is necessary to frequently remove and reapply the cosmetic layer, which is a considerable inconvenience to most women. In order to avoid this it is necessary to frequently remove and reapply the cosmetic layer, which is a considerable inconvenience to most women.

In some cases, an individual's sebum production is so high that it liquefies the cosmetic pigment layer, resulting in a rapid removal of the facial cosmetic either by physical friction/abrasion or by liquid flow. This problem is particularly acute on the eyelid and/or immediately below the eye. In order to avoid this it is necessary to frequently remove and reapply the cosmetic layer, which is a considerable inconvenience to most women.

Accordingly, there is a continuing need for cosmetic compositions that provide excellent coverage and a natural skin appearance while also concealing skin imperfections or protecting skin against damage from ultraviolet radiation. Additionally, cosmetic compositions may serve as a base for such pigmented products, or can be applied over such pigmented products, thereby increasing their durability. Alternatively, cosmetic compositions may act as pure oil absorbers without the use of any other pigmented product. Such cosmetic compositions should be resistant to the deterioration caused by sebum and thereby provide long-lasting durability that lasts the entire day without the need for continued maintenance and reapplication. Additionally, these cosmetic compositions should have a smooth, comfortable, non-oily feeling when applied to the skin. There is also a need for mild, non-irritating cosmetic compositions that ameliorate or eliminate the affects of skin disorders, and reduce the blemishes and redness associated with acne.

BRIEF SUMMARY OF THE INVENTION

The present invention includes a cosmetic fluid composition comprising a sebum-absorbing calcium silicate, and a dispersant or carrier for the calcium silicate.

The invention also includes a method of preparing a cosmetic composition wherein the calcium silicate is mixed with a cyclic silicone to form a premix, the premix is combined with one or more other cosmetic ingredients to form the fluid cosmetic composition.

The present invention also includes a method for treating facial skin comprising the steps of preparing a cosmetic composition according to claim 1, and applying the cosmetic composition to facial skin.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings.

DETAILED DESCRIPTION OF THE INVENTION

All parts, percentages and ratios used herein are expressed by weight unless otherwise specified. All documents cited herein are incorporated by reference.

By "fluid composition" it is meant a composition that contains greater than 20% by weight of one or more ingredients acceptable for use in cosmetics that are liquid at temperatures less than 100° C., such as lotions, creams, gels, semisolids, emulsions, solutions, dispersions, foams, mousses, sprays and the like.

By "casual sebum level" it is meant the natural sebum level of individuals before treatment with a sebum absorbing cosmetic.

By "coated" it is meant that the specified coating ingredient covers at least a portion of the outer surface of a particle or substrate.

Names given to chemical substances herein generally are either accepted chemical names, or are trade organization or regulatory agency approved names such as CTFA Adopted Names as listed in J. A. Wenninger et al., Eds., CTFA International Cosmetic Ingredient Dictionary, Eighth Ed., The Cosmetic, Toiletry and Fragrance Association, Washington, D.C., 2000.

The present application relates to cosmetic compositions that comprise synthetic silicates, preferably calcium silicate particles. The silicates act as absorbents to absorb the wax and lipid-based sebum material. By incorporating these calcium silicates, the cosmetic compositions provide effective, long-lasting facial cosmetic coverage that is highly resistant to the sebum-caused deterioration that results in the discoloration and fading typically experienced by conventional cosmetic compositions after a sustained period of use.

While not wishing to be limited by theory, it is believed that the calcium silicates contained in the cosmetic compositions prepared according to the present invention rapidly absorb the sebum secreted onto the surface of the skin. As discussed above, sebum secreted onto the surface of the skin helps the skin to retain its suppleness, firmness, and moistness so that it serves as an effective permeable barrier for the body. The two principal components of sebum are triglycerides and wax esters (these two components make up nearly 70 wt % of sebum). Sebum also contains other lipids, fatty acids, and cholesterols.

The high oil absorption capacity of the calcium silicates encourage the movement of the sebum into the intraparticle pores and interstices that are formed within the calcium silicates. The high surface area of the calcium silicates allows for the sebum to be easily adsorbed onto the surfaces of the silicate particles. Thus, by incorporating these silicates into the cosmetic compositions, the resulting cosmetic compositions are more resistant to deterioration by sebum and provide more attractive, durable, long-lasting wear.

It has been known that calcium silicate is useful for absorbing sebum, as described above, when incorporated into powder cosmetics. However, it was previously thought that calcium silicate was effective as a sebum-absorber only when present in dry form, such as in cosmetic powders, because the calcium silicate particulate surfaces and pores had to be free of liquid components and therefore available to absorb sebum. However, by the present invention it has now been determined that calcium silicates having a high oil absorption capacity may also be effective in fluid composition cosmetics. Indeed, the present calcium silicate particles are particularly suitable for use in fluid cosmetic compositions such as cremes or lotions. Because of their small particle size, they can be easily incorporated into a creme or lotion without giving it a gritty, uncomfortable feeling when applied to the skin.

Thus, the present cosmetic fluid compositions contain sebum-absorbing calcium silicate and also a vehicle to act as a carrier or dispersant for the sebum-absorbing calcium silicate, so as to facilitate the distribution of the calcium silicate when the composition is applied to the skin. (Suitable carriers are discussed in greater detail below.) The cosmetic fluid compositions can be in the form of a liquid, cream, gel, semi-solid, and solid types of mixtures or emulsions, all of which form a single discrete mass of a homogeneous, uniform, and non-particulate appearance. At least 20 wt % of the fluid cosmetic compositions prepared according to the present invention are composed of ingredients that are liquid at temperatures below 100° C.

Preferably the oil absorption of the sebum-absorbing calcium silicates is greater than 200 ml/100 g, preferably between 400 ml/100 g and 600 ml/100 g, most preferably around 475ml/100 g. The surface area (BET) is preferably around 150 $m^2/g$ to 600 $m^2/g$, preferably between 300 $m^2/g$ and 600 $m^2/g$, actually between 310 $m^2/g$ and 350 $m^2/g$. The particle size is preferably less than 20 microns.

These calcium silicates are most typically prepared by the reaction of a reactive silica with an alkaline earth metal reactant, preferably an alkaline earth metal oxide or hydroxide, and a source of aluminum such as sodium aluminate or alumina. Because the final properties of the silicate are dependent on the reactivity of the silica, the silica source is preferred to be the reaction product of a soluble silicate, such as sodium silicate, and amineral acid, such as sulfuric acid. Suitable synthetic amorphous alkaline earth metal silicates are manufactured by the J. M. Huber Corporation and are sold in different grades under the trademark Hubersorb®. Methods and techniques for preparing these silicas are discussed in greater detail in U.S. Pat. No. 4,557,916. Other suitable silicates are available from J. M. Huber Corporation such as sodium aluminosilicate sold under the trademark Zeolex® and sodium magnesium aluminosilicate sold under the trademark Hydrex®.

Physical characteristics of the calcium silicate used in the present invention, as well as the pertinent characteristics of other materials are given below in Table I.

TABLE I

Physical Properties of Absorbents

| Absorbent | Median particle size, μm | Specific surface area, BET, m2/g | Oil Absorption Linseed oil rub-out method, cc/100 g | Loose bulk density, g/ml |
|---|---|---|---|---|
| PolyGloss ® 90 | 0.4 | 22 | 42 | 2.6 |
| Zeofree ® 80 | 14 | 140 | 200 | 0.14 |
| Zeothix ® 265 | 4 | 250 | 220 | 0.10 |
| Cab-O-Sil ® M5 | 9 | 207 | 189 | 0.04 |
| Hubersorb ® 600 | 5 | 320 | 475 | 0.13 |
| Sebumase | 8 | 300 | 180 | 0.10 |

Polygloss® 90, a kaolin clay, Zeofree® 80 and Zeothix® 265, synthetic amorphous precipitated silicas, and Hubersorb®, 600 a calcium silicate, are available from the J. M. Huber Corporation. Cab-O-Sil® M5 synthetic amorphous fumed silica is available from the Cabot Corporation, Bellrica, Mass. Sebumase is a Magnesium Aluminum Silicate distributed by U.S. Cosmetics Corporation, Dayville, Conn.

The effectiveness of the calcium silicate, compared to other absorbents in absorbing hydrophobic substances (such as sebum) can be seen in Table II, below

TABLE II

Oil Absorption Capacity for different hydrophobic substances

| Absorbent | Glycerol cc/100 g | Synthetic sebum cc/100 g | Squalane cc/100 g |
|---|---|---|---|
| Corn Starch | 20 | 29 | 30 |
| PolyGloss 90 | 40 | 45 | 65 |
| Zeosyl ® TG80 | incompatible | 147 | 169 |
| Zeofree ® 80 | 160 | 189 | 206 |
| Zeithix ® 265 | 185 | 202 | 242 |
| Cab-O-Sil ® M5 | 188 | 227 | 320 |
| Hubersorb ® 600 | 245 | 329 | 373 |
| Sebumase | 221 | 179 | 267 |

Zeosyl® TG80, synthetic amorphous precipitated silica treated with polydimethylsiloxane is available from J. M.

Huber Corporation. Synthetic sebum is a blend of oils typically found in human sebum, except that the higher molecular weight waxy compounds typically found in human sebum are omitted so that the synthetic sebum will be in liquid form at room temperature. The composition of synthetic liquid sebum is listed in Table III below.

TABLE III

Synthetic Sebum Composition

| Ingredient | Weight, g |
|---|---|
| Olive Oil | 100 |
| Oleic acid | 50 |
| Linolenic Acid | 25 |
| Squalane | 25 |
| Coconut Oil | 75 |

Squalane, $C_{30}H_{62}$ (Tetracosane or 2,6,10,15,19,23-hexamethyl—), is (at room temperature) a liquid saturated hydrocarbon that functions as a natural emollient and is known for its unusual ability to increase the rate, depth, and extent of penetration of topical agents from medicated ointments. The squalane used in the present example was purchased from Arista Industries, Wilton, Conn. (Squalane should be distinguished from Squalene, $C_{30}H_{50}$, an unsaturated aliphatic hydrocarbon that is a natural component of human sebum but may also be obtained from other sources such as vegetable and fish oils. In fact, Squalane is produced by the hydrogenation of Squalene)

Where mentioned in this application, the BET surface area was determined by the BET nitrogen absorption method of Brunaur et al., as reported in the J. Am. Chem. Soc. 60, 309 (1938). Bulk density is determined by weighing 100.0 grams product into a 250-mL graduated cylinder and recording the volume occupied.

The oil absorption properties shown in table I (and throughout this application) is measured with the rubout method. In this test, oil is mixed with a silica and rubbed with a spatula on a smooth surface until a stiff putty-like paste is formed. By measuring the quantity of oil required to have a paste mixture, which will curl when spread out, one can calculate the oil absorption value of the metasilicate, the value which represents the volume of oil required per unit weight of silica to completely saturate the metasilicate absorptive capacity. Calculation of the oil absorption value was done according to equation (I):

$$\text{Oil absorption} = \frac{\text{ml oil absorbed}}{\text{weight of silicate, grams}} \times 100 \quad (I)$$

$$= \text{ml oil}/100 \text{ gram silicate}$$

Particle size is determined using a Model LA-910 laser light scattering instrument available from Horiba Instruments, Boothwyn, Pa. A laser beam is projected through a transparent cell which contains a stream of moving particles suspended in a liquid. Light rays which strike the particles are scattered through angles which are inversely proportional to their sizes. The photodetector array measures the quantity of light at several predetermined angles. Electrical signals proportional to the measured light flux values are then processed by a microcomputer system to form a multichannel histogram of the particle size distribution.

As can be seen in Table II, calcium silicate absorbs a far greater amount of each of these hydrophobic substances than any of the other absorbents listed in Table II. This performance is indicative of a structure that will be highly effective as a sebum micro-absorber in a cosmetic composition. Cosmetic compositions prepared according to the present invention comprise about 0.1 wt % to about 25 wt %, preferably about 1 wt % to about 10 wt % of the sebum-absorbing calcium silicate.

As mentioned above, in addition to a sebum-absorbing calcium silicate, the present fluid cosmetic compositions also contain a vehicle to act as a carrier or dispersant for the calcium silicate, so as to facilitate the distribution of the calcium silicate when the composition is applied to the skin.

Vehicles other than or in addition to water can include cosmetic astringents, liquid or solid emollients, emulsifiers, film formers, propellants, skin-conditioning agents, humectants, skin protectants, solvents, solubilizing agents, suspending agents, surfactants, sunscreen agents, ultraviolet light absorbers, waterproofing agents, viscosity increasing agents 30 (aqueous and nonaqueous), waxes, wetting agents, and the like.

The cosmetically acceptable vehicle will usually form from 50% to 99.9%, preferably from 80% to 90% by weight of the composition, and can, in the absence of other cosmetic adjuncts, form the balance of the composition. Preferably, the vehicle is at least 20 wt. % water, by weight of the vehicle. Preferably, water comprises at least 15 wt. % of the inventive composition, most preferably from 60 to 75 wt. % of the composition.

An oil or oily material may be present, together with one or more emulsifiers to provide either a water-in-oil emulsion or an oil-in-water emulsion, depending largely on the average hydrophilic-lipophilic balance (HLB) of the emulsifiers employed. This also includes multiple emulsions: water-in-oil-in water or an oil-in-water-in oil emulsions. The emulsions may contain any of a number of desired "active" ingredients, including skin colorants, drug substances (such as anti-inflammatory agents, antibiotics, topical anesthetics, antimycotics, keratolytics, etc.), skin protectants or conditioners, humectants, ultraviolet radiation absorbers, sunless tanning agents and the like, depending on the intended uses for the formulations.

The preferred vehicle is an emulsion containing water in amounts ranging from about 15 to 95 weight percent, preferably from about 45 to 75 percent, most preferably from about 60 percent to about 75 percent.

Suitable emulsifiers are those known in the art for producing oil-in-water and/or water-in-oil type emulsions. Particularly preferred emulsifiers are PEG-8 Distearate available as Emerest 2712 from Henkel; Sorbitan Sesquioleate, available as Arlacel 83 and Arlacel C., Steareth-21 available as Brij 721, and Steareth-2 available as Brij 72, all from ICI Surfactants; TEA-Stearate, available as Cetasal from Gattefosse S. A; neutralized cetyl phosphate, as Amphisol A from LaRoche; Acrylate/C10-C.30alkyl acrylate cross polymer of C10-30alkyl acrylates and one or more monomers of acrylic acid, methacrylic acid or one of their simple esters crosslinked within allyl ether of sucrose or an allyl ether of pentaerythritol, available as Pemulen TR from B. F. Goodrich; and Cetyl Dimethicone Copolyol available as Abil EM90 from Goldschmidt Chemical Corp. The amount of emulsifier used in the present invention is present in an amount of about 0.1 to about 10% by weight, preferably about 0.5 percent to about 5 percent by weight, most preferably about 2 percent to about 4 percent by weight In addition to the calcium silicate and the silicate vehicle, the present cosmetic compositions will also comprise one or more dermatologically acceptable cosmetic ingredients. For example, the present compositions may include sunscreens. Sunscreens include those materials commonly employed to block ultraviolet light. Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. The exact amount of sunscreen employed in the emulsions can vary depending upon the degree of protection desired from the sun's UV radiation.

Emollients are often incorporated into cosmetic compositions of the present invention. Levels of such emollients may range from 0.5% to 50%, preferably between 5% and 30% by weight of the total composition. Emollients may be classified under such general chemical categories as esters, fatty acids and alcohols, polyols and hydrocarbons. Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, and stearyl oleate. Preferred esters include coco-caprylate/caprate (a blend of coco-caprylate and coco-caprate), propylene glycol myristyl ether acetate, diisopropyl adipate and cetyl octanoate. Suitable fatty alcohols and acids include those compounds having from 10 to 20 carbon atoms. Especially preferred are such compounds such as cetyl, myristyl, palmitic and stearyl alcohols and acids. Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers. Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol from the B. F. Goodrich Company. Gums may be employed such as xanthan, carrageenan, gelatin, karaya, pectin and locust beans gum. Under certain circumstances the thickening function may be accomplished by a material also serving as a silicone or emollient. For instance, silicone gums in excess of 10 centistokes and esters such as glycerol stearate have dual functionality.

Mineral fillers or extenders may be incorporated into the cosmetic composition of the invention. These include chalk, talc, kaolin, mica, sericite, starch, smectite clays, chemically modified magnesium aluminum silicate, organically modified montmorillonite clay, hydrated aluminum silicate, fumed silica, precipitated silica, colloidal silica, silica gel, hydrotalcite, corn starch, aluminum starch octenyl succinate and mixtures thereof.

Other adjunct minor components may also be incorporated into the cosmetic compositions, such as skin feel components. Skin feel improving components, which provide good skin feel characteristics such as silica, in particular spherical silica, and silica microbeads, such as SB 150 sold by Myoshi Kasei; glass and ceramic beads sold by 3M under the name "Macrolite"; metal soaps derived from an organic carboxylic acid having from 8 to 22 carbon atoms for example zinc, magnesium or lithium stearate, zinc laurate or magnesium myristate; powders formed from non-expanded synthetic polymers, such as those formed from polyethylene, polystyrene, polyesters, polyamides (for example, Nylon or poly-.beta.-alanine); acrylate copolymers (for example, the microporous microspheres sold by Dow Corning as"Polytrap"), polymethacrylic acid, polystyrene or Teflon, such as "Fluon"; expanded powders, such as hollow microspheres made of thermoplastics, in particular the microspheres sold as "Expancel" by Kemanord Plast or as "Micropearl F 80 ED" by Matsumoto; powders formed from natural organic materials, such as maize, wheat or rice starches, which may or may not be crosslinked, such as the powders formed from starch crosslinked by octenylsuccinic anhydride sold under the name "Dry-Flo" by National Starch; silicone resin microbeads, such as those sold as "Tospearl" by Toshiba Silicone, and their mixtures. These ingredients may include coloring agents, opacifiers and perfumes. Amounts of these other adjunct minor components may range anywhere from 0.001% up to 30% by weight of the composition.

Other suitable ingredients include sebum-absorbing materials such as starch, polyethylene, nylon, boron nitride, mica, sericite, kaolin, polymer powders including natural, synthetic, and semi-synthetic cellulose, fluorocarbon resins, polypropylene, modified starches of cellulose acetate, particulate cross-linked hydrophobic acrylate and methacrylate copolymers.

Also suitable are cosmetically acceptable color pigments such as iron oxides, ultramarine blue, Prussian blue, manganese violet, bismuth oxychloride and FDA sanctioned CI pigments; pearling pigments (or nacreous pigments) such as bismuth oxychloride, guanine and titanium composite materials; and cosmetic preservatives such as trisodium EDTA, phenoxyethanol, ethyl alcohol, methylparaben, propylparaben, butylparaben, ethylparaben, potassium sorbate, diazolidinyl urea, and similar such compounds.

Other adjunct minor components may also be incorporated into the cosmetic compositions. These ingredients may include coloring agents, opacifiers and perfumes. Amounts of these adjunct minor components may range anywhere from 0.001% up to 20% by weight of the composition.

In another embodiment of the present invention, the fluid cosmetic compositions additionally contain cyclic silicones. Preferably, the cyclic silicones are deposited on the surface of the calcium silicate particles so that the cyclic silicones coat the calcium silicate particles. Typically, the cyclic silicones are mixed with the calcium silicate thereby depositing the cyclic silicones onto the calcium silicate particles and forming a premix. The premix is then combined with the other dermatologically-acceptable cosmetic ingredients to form a fluid cosmetic composition. Suitable cyclic silicones include volatile silicone polymers such as cycloheptasiloxane, cyclohexasiloxane, cyclopentasiloxane, cyclotetrasiloxane, cyclotrisiloxane and Dimethicone.

Cosmetic compositions according to the present invention may be prepared in any form which is suitable for topical application to the skin, for example, solutions, colloidal dispersions, emulsions, suspensions, creams, lotions, gels, foams, mousses, sprays, and the like. Preferably the present cosmetic compositions are prepared in the form of a gel or emulsion. These cosmetic compositions may then be packaged in the form of a cream, solid stick, gel or lotion and sold to consumers.

The invention will now be described in more detail with respect to the following, specific, non-limiting examples.

EXAMPLE 1

In-vivo clinical trials were done to compare the performance of two pressed facial powders. A facial pressed powder was prepared according to the present invention and is set forth as Example 1 of Table IV below along with a control for comparative purposes.

TABLE II

| Ingredient | Example 1 | Control 1 |
| --- | --- | --- |
| Talc, g | 63.2 | 63.5 |
| Mg Stearate, g | 3.98 | 4.00 |
| Nylon-12, g | 1.99 | 2.00 |
| Titanium Dioxide, g | 7.96 | 8.00 |
| Iron Oxide, g | 17.91 | 18.00 |
| absorbent calcium silicate, g | 0.50 | 0.00 |
| Methylparaben, g | 0.20 | 0.20 |
| Propylparaben, g | 0.20 | 0.20 |
| Imidazolidinyl Urea, g | 0.10 | 0.10 |
| PEG-4 Diheptanoate, g | 3.98 | 4.00 |

Clinical testing was performed with lipid-absorbent Sebutape® strips available from Cuderm Corporation, Dallas, Tex. The testing was performed on 20 healthy subjects of between 20 and 60 years of age. The sebum casual levels were derived from a set of Sebutape® strip readings made exactly one hour after the skin of the forehead had been thoroughly cleaned by wiping with pads soaked in 70% ethanol. After the alcohol evaporated, the strip was applied to the forehead with moderate pressure and removed after 10 seconds. The subjects were ranked as having untreated skin types ranging from "dry" to "oily". Dry skin has low sebum concentration, corresponding to a "light" Sebutape reading of 1 point, expressed in arbitrary units. Oily skin has a high sebum concentration, corresponding to a "dark" Sebutape reading 5 points. This assured a distribution of skin types would be available for the clinical testing.

Prior to the testing of the cosmetic compositions, the skin surface at the nose area of 17 available test subjects (selected from the 20 subjects evaluated above) was cleaned with ethanol-soaked pads. After a 1 minute pause to allow the ethanol to evaporate the group was split into two test groups and dry cosmetic powder described above in Table IV was applied to a cotton pad and transferred directly to the cleaned skin by lightly dabbing the pad. The example 1 powder (which is prepared according to the present invention) was applied to nine subjects and the control 1 powder, which is free of calcium silicate and is representative of prior art powders, was applied to eight subjects. Following a period of two hours, Sebutape lipid-absorbent strips were pressed firmly against the test area of the skin for 10 seconds to determine the amount of sebum liberated from the skin at the test area. After a two hour rest period, the procedure was repeated with each subject using the alternate cosmetic test powder. Throughout the period of the study, both the outside temperature and that inside the clinic were between 15 and 21° C.

The test strips were collected from both trials and converted to binary digital images using a flatbed scanner, and digital data obtained through the use of the scanner analyzed using ImagePro Plus 3.0 software to quantify the total spot area (number of dark pixels) on the lipid-absorbent strips. The greater the total dark spot area, the higher the levels of sebum secreted from infundibular reservoirs, and thus higher levels of sebum concentration at the skin surface. In 12 of the 17 subjects, lower sebum concentrations were measured on skin surfaces that had been treated with the example 1 cosmetic powder. A 10% improvement is seen with Example 1 powder containing calcium silicate over the control 1 powder.

Figure 1:
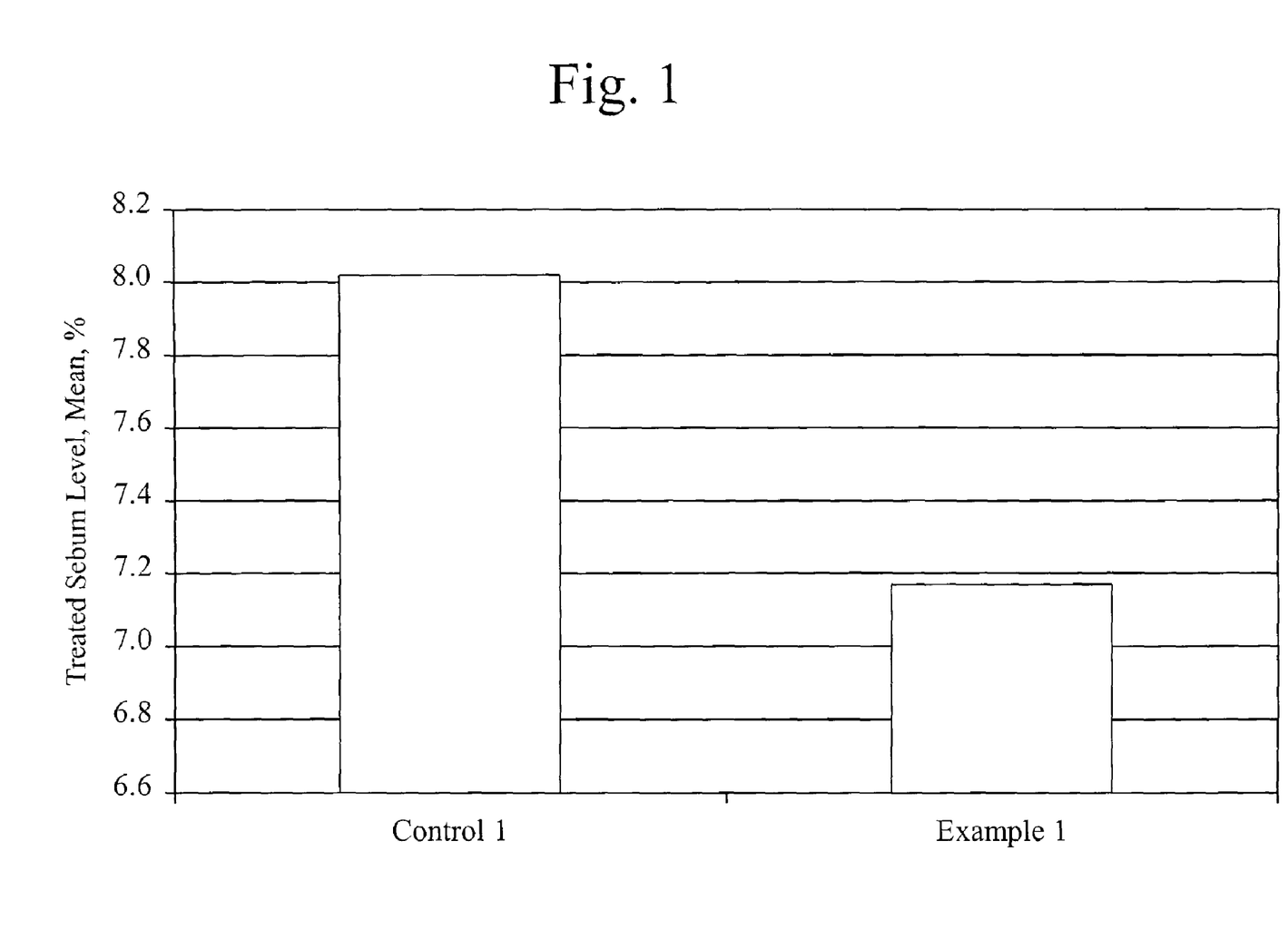
FIG. 1 is a graph showing the sebum absorption comparison of Example 1.

FIG. 1 shows the sebum absorption of example 1 powder containing calcium silicate and the sebum absorption of the control 1 powder, which contained no calcium silicate. The sebum level for each formulation is an average of all the test subjects calculated from Sebutape pixel spot area measurements, calculated according to equation (II):

$$\text{Mean sebum level} = \frac{\sum (1 - \text{treated}/\text{total area}) * 100)}{n} \quad \text{(II)}$$

where n is the number of subjects.

EXAMPLE 2

The performance of the cosmetic compositions in the form of lotions were prepared according to the present invention was evaluated in a clinical test of ten healthy subjects having oily skin. The Example 2 cosmetic lotion is prepared according to the present invention, while the Example 2 Control cosmetic lotion is a conventional lotion, which contains no calcium silicate. The lotion formulations tested are set forth in Table V below.

TABLE V

| Ingredient | Example 2 lotion | Example 2 Control lotion |
| --- | --- | --- |
| Kelzan M Resin, g | 0.3 | 0.31 |
| CMC 7MF, g | 0.92 | 0.95 |
| calcium silicate, g | 5.00 | 0.00 |
| Water, g | 93.88 | 98.74 |

Kelzan M Resin is xanthan gum available from CP Kelco of Chicago, Ill. CMC 7MF is carboxymethyl cellulose available form Aqualon Corporation of Wilmington, Del. The calcium silicate is Hubersorb 600.

Evaluations of sebum concentration were made by testing alcohol cleaned skin, allowing two hours to elapse between the application of the lotion and the measurements. Cosmetic lotions were applied directly to one side of the forehead. The untreated area on the adjacent side of the forehead was used for the casual sebum level. Measurements were made using Sebutape and the ImagePro Plus software as described above. The equations used to calculate these results are given in equation III (Example 2 Control) and equation IV (Example 2).

$$\text{Sebum level} = \frac{\sum (1 - \text{untreated}/\text{total area}) * 100}{n} \quad \text{(III)}$$

$$\text{Sebum level} = \frac{\sum (1 - \text{treated}/\text{total area}) * 100)}{n} \quad \text{(IV)}$$

Where, treated and untreated are the spot area measurements (in pixels) darkened by sebum and total area is the total available pixel count for the entire test area, to allow a percent of the whole to be determined.

Figure 2:
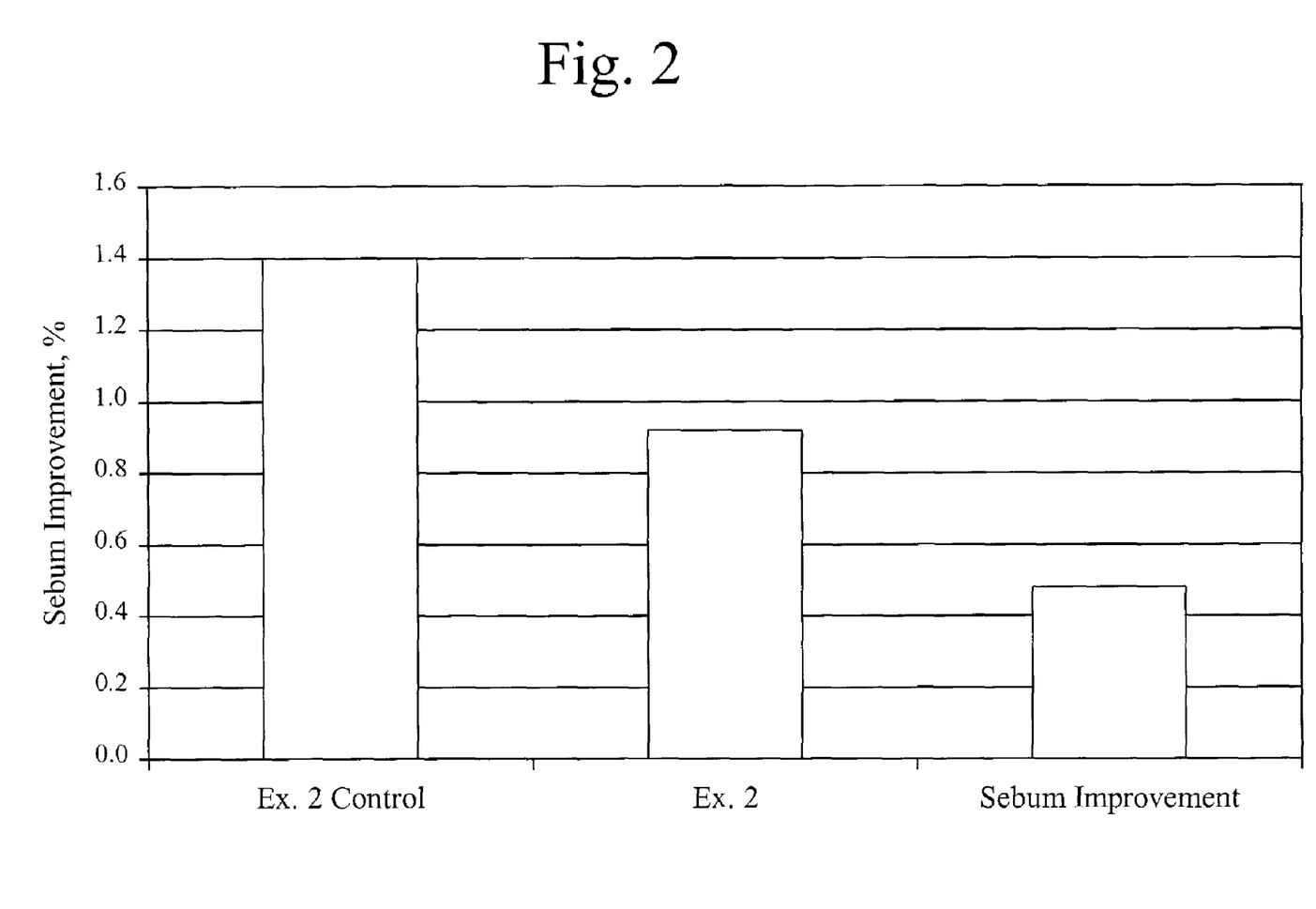
FIG. 2 is a graph showing the sebum absorption comparison of Example 2.

The results of this clinical test measuring sebum shown in FIG. 2 demonstrate 36% sebum improvement for the Example 2 cosmetic lotion, which is prepared according to this invention.

EXAMPLE 3

The performance of the cosmetic compositions prepared according to the present invention in a simple water/alcohol cosmetic preparation was evaluated in a clinical test of fifteen subjects having oily skin. Example 3 is a conventional water/alcohol cosmetic preparation, Example 3 Control is also a water/alcohol preparation additionally containing witch hazel astringent and Example 3 blank contains neither calcium silicate nor witch hazel. All three composition formulations are given in Table VI, below. An astringent reduces sebum secretion by closing the skin pores. This example evaluates the performance of sebum-absorbing calcium silicate versus witch hazel astringent.

TABLE VI

| Ingredient | Example 3 | Example 3 control | Example 3 blank |
|---|---|---|---|
| Glycerin, g | 2 | 2 | 2 |
| Isopropyl Alcohol, g | 20 | 20 | 20 |
| calcium silicate, g | 5.00 | 0.00 | 0 |
| Witch Hazel, g | 0.0 | 10.0 | 0 |
| Water, g | 73 | 68 | 78 |

Clinical testing was performed with lipid-absorbent Sebutape® on 15 healthy subjects of between 20 and 60 years of age for two consecutive days. Foreheads were thoroughly cleaned by wiping with pads soaked in 70% ethanol and the subjects were treated with the simple water/alcohol cosmetic preparation of this invention. The water/alcohol cosmetic was applied using a sterile cotton pad. After 2 hours, Sebutape was used to measure the sebum concentration of the treated area, while the untreated area on the opposite side was used for the casual sebum level. Following a minimum of 4 hours, the subjects were then tested in the same manner described above with the other compositions described in Table VI above.

Figure 3:
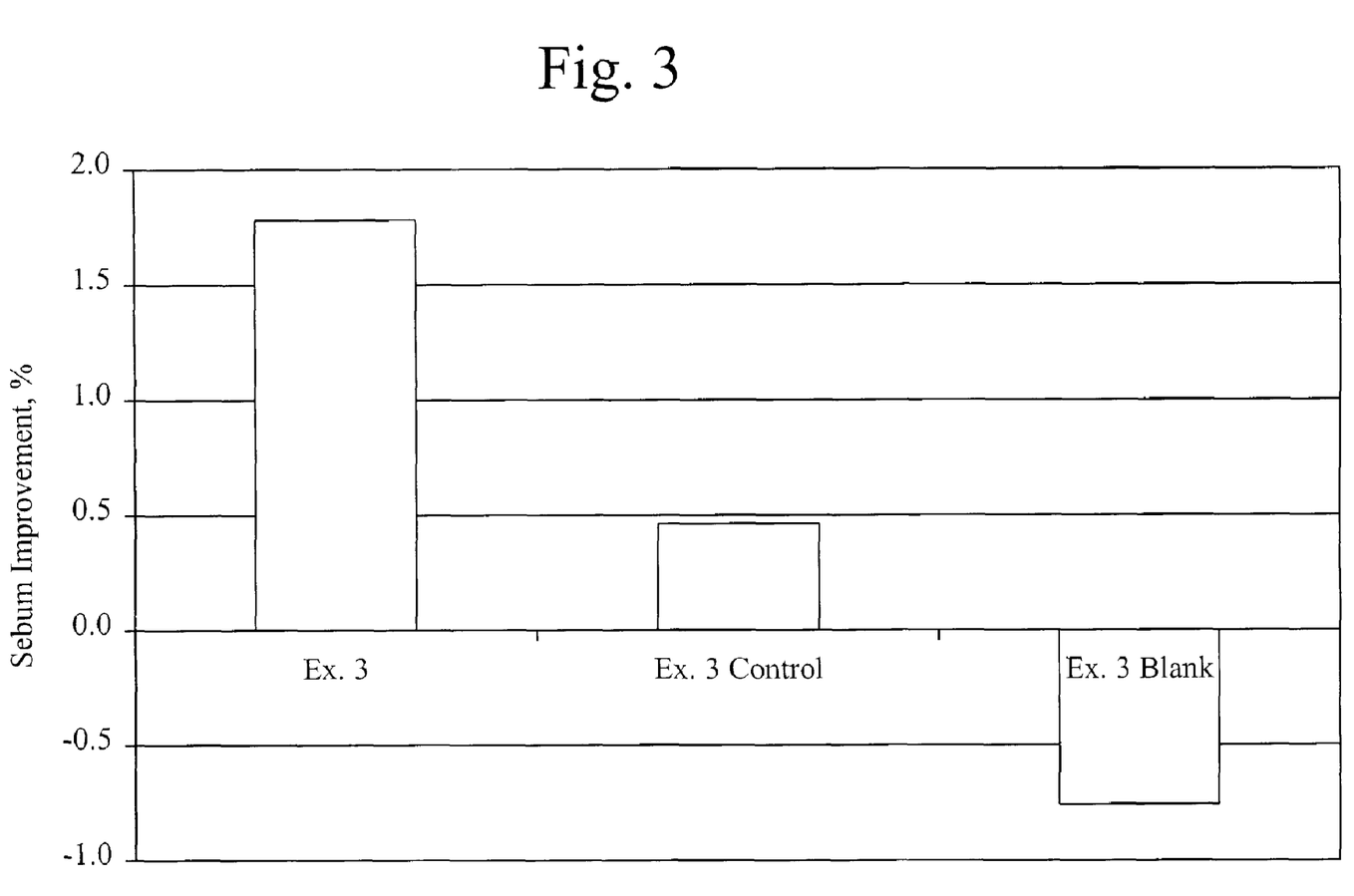
FIG. 3 is a graph showing the sebum absorption comparison of Example 3.

FIG. 3 is a graphical representation of the results of the clinical tests of Example 3, Example 3 Control and Example 3 blank. For this set of clinical trials, equation V is used to compare the average performance of each formulation to the average of the subjects' casual sebum level:

$$\text{Sebum improvement} = \frac{\Sigma[(1 - \text{untreated/total area}) \times 100 - (1 - \text{treated/total area}) \times 100]}{n} \quad (V)$$

EXAMPLE 4

Oil-in-water emulsion based lotions containing calcium silicate were prepared according to the present invention (the "Example 4" emulsions). A conventional oil-in-water emulsion with no calcium silicate was also prepared as the Example 4 control lotion. These formulations are given in Table VII.

TABLE VII

| Tradename | INCI Name | Example 4 control | Example 4 |
|---|---|---|---|
| Oil Phase: | | | |
| Abil EM90, g | Cetyl Dimethicone Copolyol | 2.00 | 2.00 |
| Ultrapure SAP Grade, g | Stearyl Alcohol | 0.60 | 0.60 |
| Rita CA Cetyl Alcohol, g | Cetyl Alcohol | 0.90 | 0.90 |
| Abil Wax 9801, g | Cetyl Dimethicone | 4.00 | 4.00 |
| Powder Phase: | | | |
| Hubersorb 600, g | Calcium Silicate | 0.00 | 5.00 |
| Water Phase: | | | |
| Deionized Water, g | Water (Aqua) | 91.50 | 86.50 |
| Brij 721, g | Steareth-21 | 1.00 | 1.00 |

Rita CA Cetyl Alcohol is available from Rita Corporation, Woodstock, Ill.; Abil Wax 9801 and Abil EM90 are available from Goldschmidt Chemical Corporation, Hopewell, Va.; Brij 721 is available from Uniquema, Wilmington, Del.; Ultrapure SAP Grade is available from Ultra Chemical, Inc., New Jersey.

An oil-in-water emulsion was prepared from the ingredient amounts given in Table VII by separately preparing a water phase and an oil phase, then combining the two phases to form an emulsion. The water phase is prepared by weighing water into an appropriately sized beaker and heating to 65–70° C., while keeping the beaker covered. Thereafter, Brij 721 is added to the heated water. The calcium silicate was added to the prepared water phase, while homogenizing with a Silverson Mixer. Mixing was continued, while the oil phase was prepared. To prepare the oil phase, combine all oil phase ingredients in a separate beaker and mix with a spatula until this oil phase appears uniform and has reached a temperature of between 70–75° C. Add the oil phase to the water phase, while continuing to homogenize, then decrease speed of mixing. After oil addition is complete, mixing was continued at a slow speed until the emulsion reached 50° C. Then it was cooled while stirring with a Lightnin mixer until the batched reached a temperature of 30° C. Thereafter, cooling was continued while stirring with a spatula until the batch reached room temperature.

Figure 4:
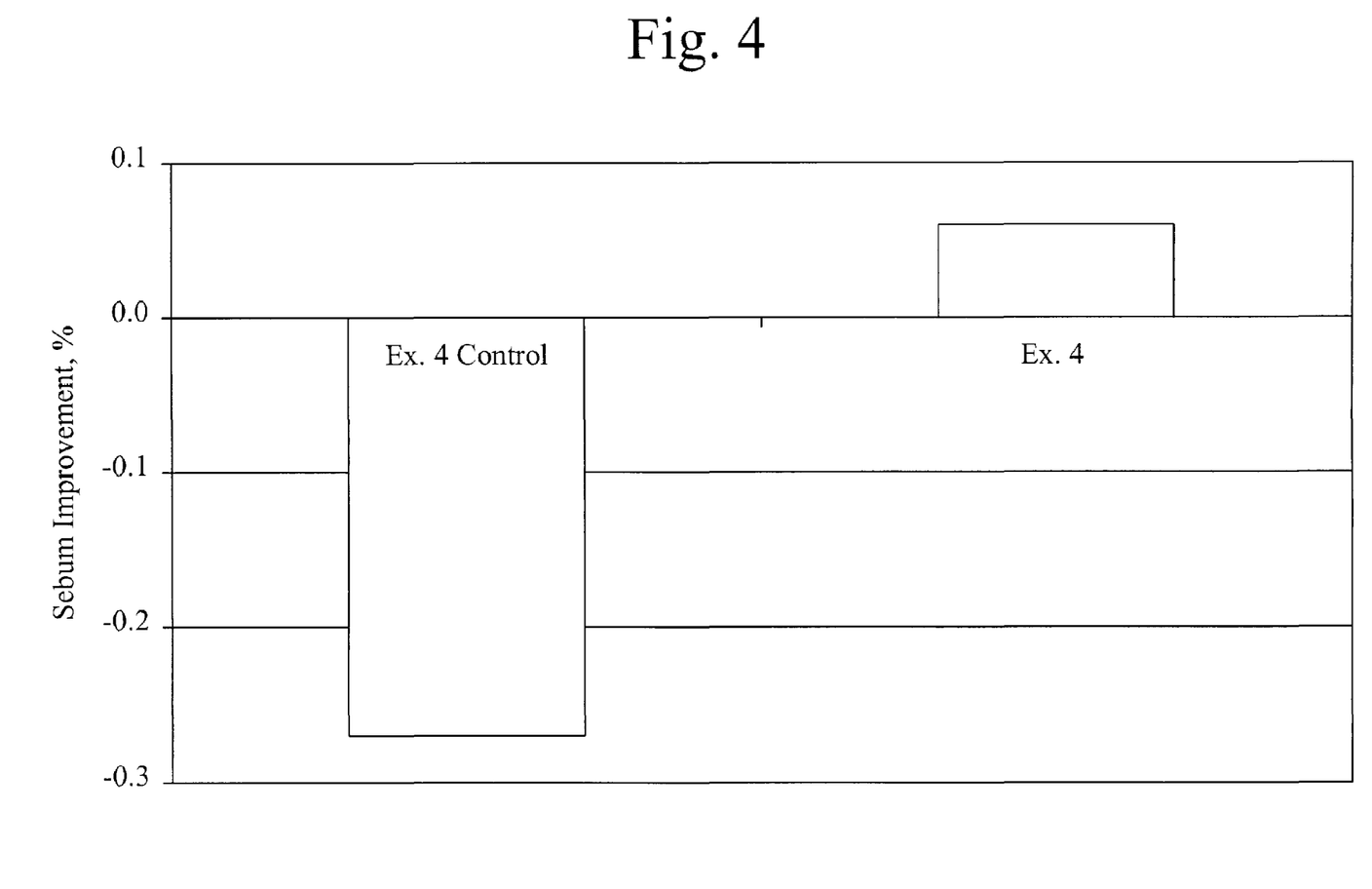
FIG. 4 is a graph showing the sebum absorption comparison of Example 4.

Foreheads of the test subjects were thoroughly cleaned by wiping with pads soaked in 70% ethanol and, after allowing the alcohol to evaporate, one side of the subjects' forehead was treated with the Example 4 lotion, which contains calcium silicate. The Example 4 lotion was applied using a sterile cotton pad. After 2 hours, Sebutape was used to measure the sebum concentration of the treated area, while the untreated area on the opposite side was used for the casual sebum level. After 4 hours, the same subjects were treated with the Example 4 Control lotion and Sebutape measurements were again made, as previously described. It is seen in FIG. 4 that the Example 4 control lotion actually contributed to the levels of sebum detected on the subject's skin, thus resulting in a negative "sebum improvement". By contrast, the Example 4 lotion, which contained calcium silicate, did not contribute to the sebum levels and actually showed minor improvement over the casual sebum level.

The performance of cosmetic lotions prepared according to the present invention was tested. The Example 5 lotion composition set forth below in Table VIII was prepared according to the present invention, containing calcium silicate which had been previously treated with cyclopentasiloxane. Specifically, a calcium silicate premix was formed by mixing 75.7% SF1202 (cyclopentasiloxane from GE Silicones, General Electric Corporation, Waterford, N.Y.) with 24.3% calcium silicate. The cyclic silicone treatment protects the calcium silicate pores during manufacture making them available for sebum absorption after application to skin.

TABLE VIII

| Ingredient | Example 5 |
| --- | --- |
| Kelzan M resin, g | 0.30 |
| CMC 7MF, g | 0.95 |
| Calcium silicate premix, g | 10 |
| Water, g | 82.75 |

Figure 5:
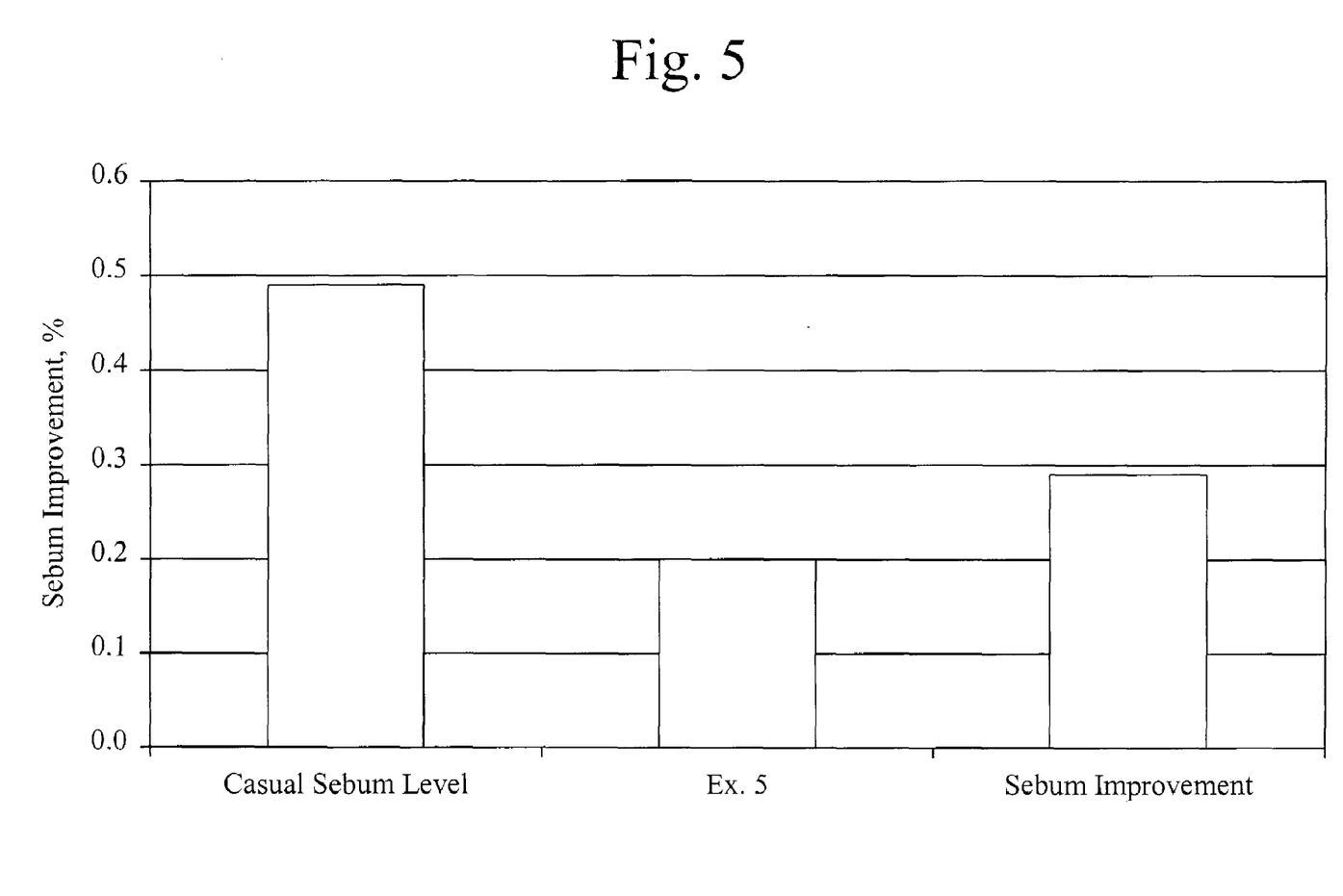
FIG. 5 is a graph showing the sebum absorption comparison of Example 5.

Ten healthy subjects had their forehead skin cleaned with ethanol as described earlier. After the ethanol evaporated, the lotion described in Table VIII was applied to half of the forehead with the other half used to determine casual sebum levels. After 2 hours, Sebutape readings were measured, as described in previous examples. It is seen in FIG. 5 that there is a 40% improvement in sebum levels for the Example 5 lotion, which contains the cyclopentasiloxane-treated calcium silicate.

It will be appreciated by those skilled in the art that changes could be made to the embodiments described above without departing from the broad inventive concept thereof It is understood, therefore, that this invention is not limited to the particular embodiments disclosed, but it is intended to cover modifications within the spirit and scope of the present invention as defined by the appended claims.

We claim:

1. A method of preparing a fluid cosmetic composition comprising a sebum-absorbing calcium silicate wherein said composition is in a form selected from the group consisting of a water-based formulation, a water/alcohol-based formulation, and an emulsion, wherein if said composition is in the form of an emulsion, then said sebum-absorbing calcium silicate is present within the water phase of said emulsion; wherein said cosmetic composition further comprises at least one cosmetic ingredient selected from the group consisting of: skin feel components, additional sebum absorbing materials, cosmetic preservatives, mineral fillers and extenders, color pigments, sunscreens, emollients, thickeners, opacifiers, and perfumes; and wherein said sebum-absorbing calcium silicate includes a cyclic silicone deposited thereon prior to incorporation within said composition; said method comprising the steps of:

a) providing calcium silicate in particulate form;

b) mixing said particulate calcium silicate with a cyclic silicone to form a premix wherein said cyclic silicone is deposited on the particles of calcium silicate; and c) combining the premix of step "b"with at least one solvent and at least one of said cosmetic ingredients to form said fluid cosmetic composition; wherein the cyclic silicone is selected from cycloheptasiloxane, cyclohexasiloxane, cyclopentasiloxane, cyclotetrasiloxane, and cyclotrisiloxane.

* * * * *